United States Patent

Guala

[11] Patent Number: 6,129,330
[45] Date of Patent: Oct. 10, 2000

[54] ROLLER CLAMP FOR REGULATING FLUID FLOW THROUGH AN ELASTICALLY DEFORMABLE TUBING

[75] Inventor: Gianni Guala, Turin, Italy

[73] Assignee: Industrie Borla Spa, Mancalieri, Italy

[21] Appl. No.: 09/369,338

[22] Filed: Aug. 6, 1999

[30] Foreign Application Priority Data

Sep. 9, 1998 [IT] Italy .................... TO98A0758

[51] Int. Cl.⁷ .................... F16K 7/04; A61M 39/28
[52] U.S. Cl. .................... 251/6
[58] Field of Search .................... 251/4, 6; 222/101; 604/250

[56] References Cited

U.S. PATENT DOCUMENTS

| | | | |
|---|---|---|---|
| 3,918,675 | 11/1975 | Forberg | 251/6 |
| 3,960,149 | 6/1976 | Bujan | 251/6 |
| 4,270,725 | 6/1981 | Scott et al. | 251/6 |
| 4,475,708 | 10/1984 | Becker, Jr. | 251/6 |
| 4,725,037 | 2/1988 | Adelberg | 251/6 |
| 4,856,755 | 8/1989 | Clarke | 251/6 |
| 4,869,721 | 9/1989 | Karpisek | 251/6 |
| 4,974,811 | 12/1990 | Ishida | 251/6 |
| 5,014,962 | 5/1991 | Adelberg | 251/6 |
| 5,190,079 | 3/1993 | Nakada | 251/6 |

*Primary Examiner*—Kevin Shaver
*Assistant Examiner*—Eric Keasel
*Attorney, Agent, or Firm*—Young & Thompson

[57] ABSTRACT

Roller clamp for regulating a fluid flow through an elastically deformable tubing, comprising a generally channel-shaped body and a roller longitudinally movable in a guided fashion parallel to a clamping surface of the bottom wall of the body so as to clamp the elastically deformable tubing. Longitudinal lateral recesses are formed between the clamping surface and the lateral walls of the body, at least along part of a longitudinal central groove having a decreasing section of the bottom wall, which are designed to accommodate elastic expansion of the tubing being clamped.

8 Claims, 4 Drawing Sheets

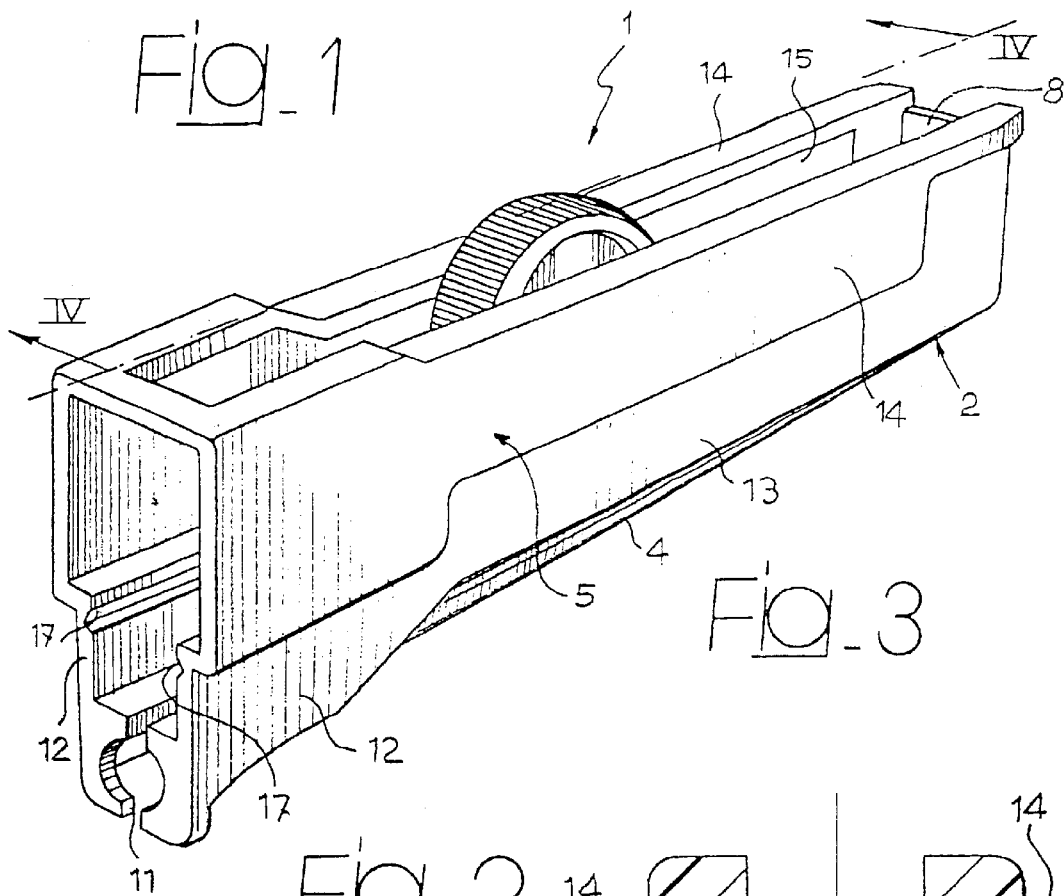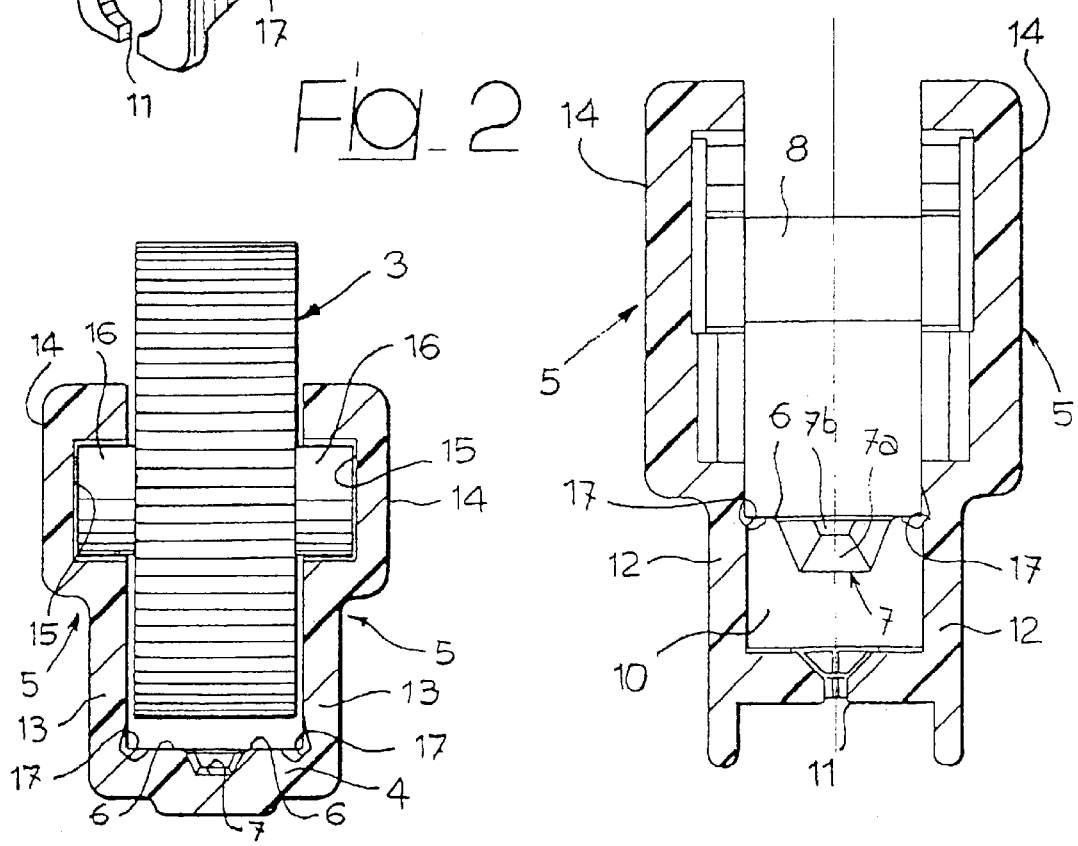

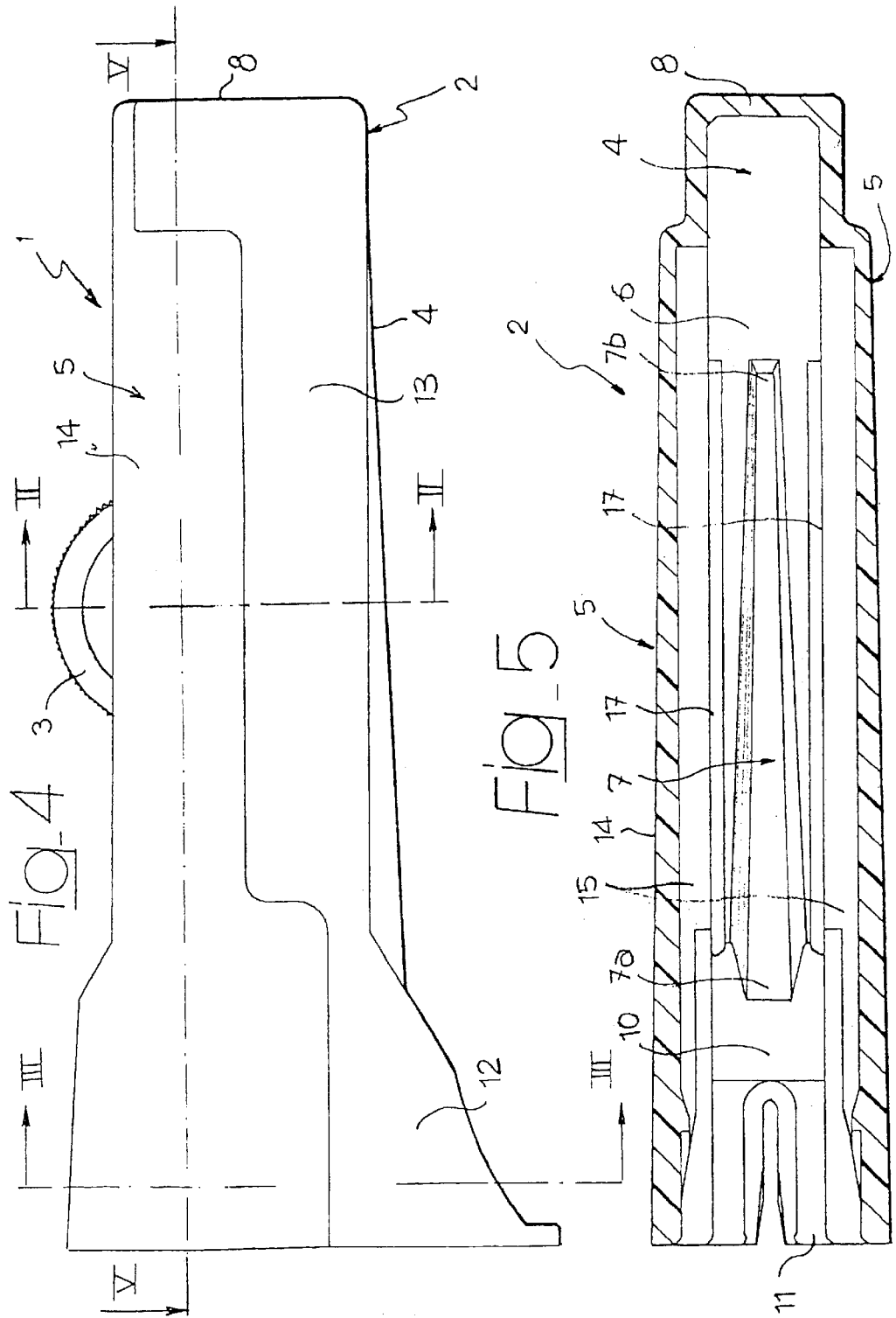

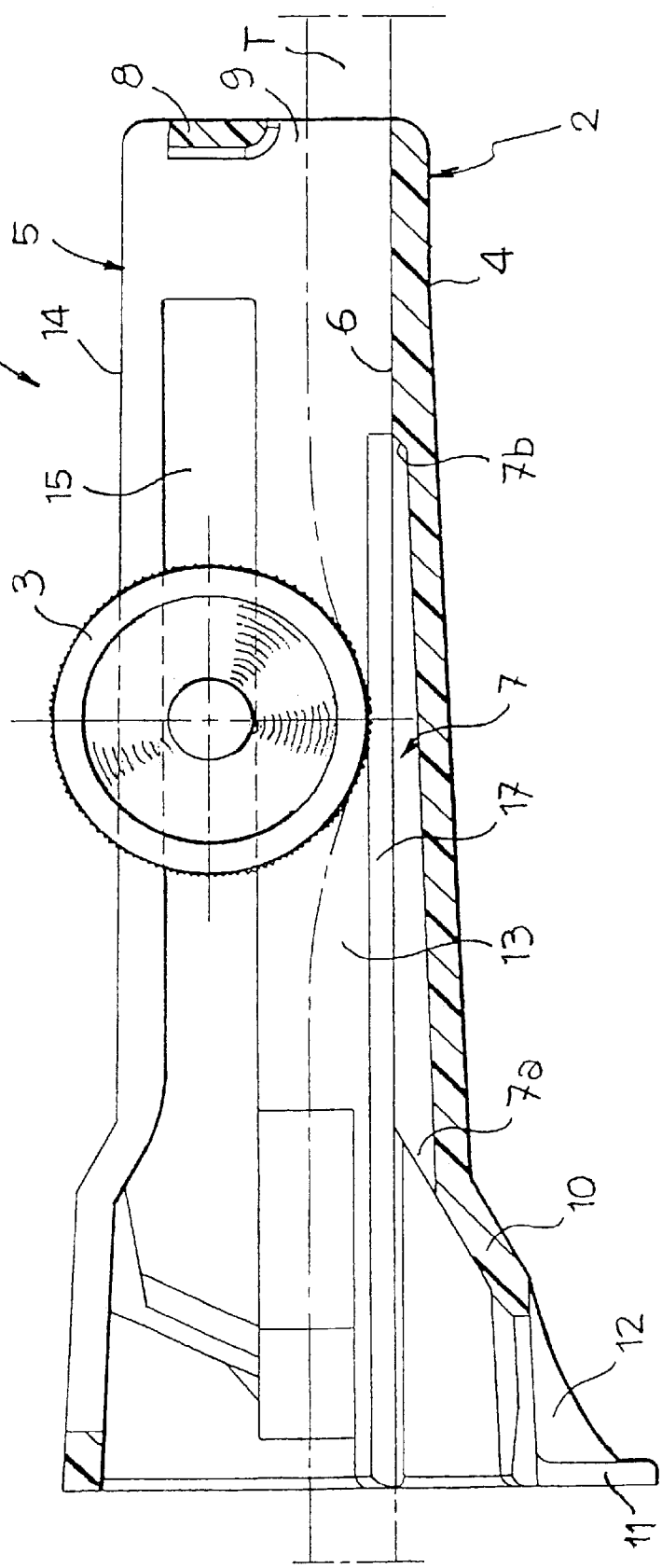

Fig_7
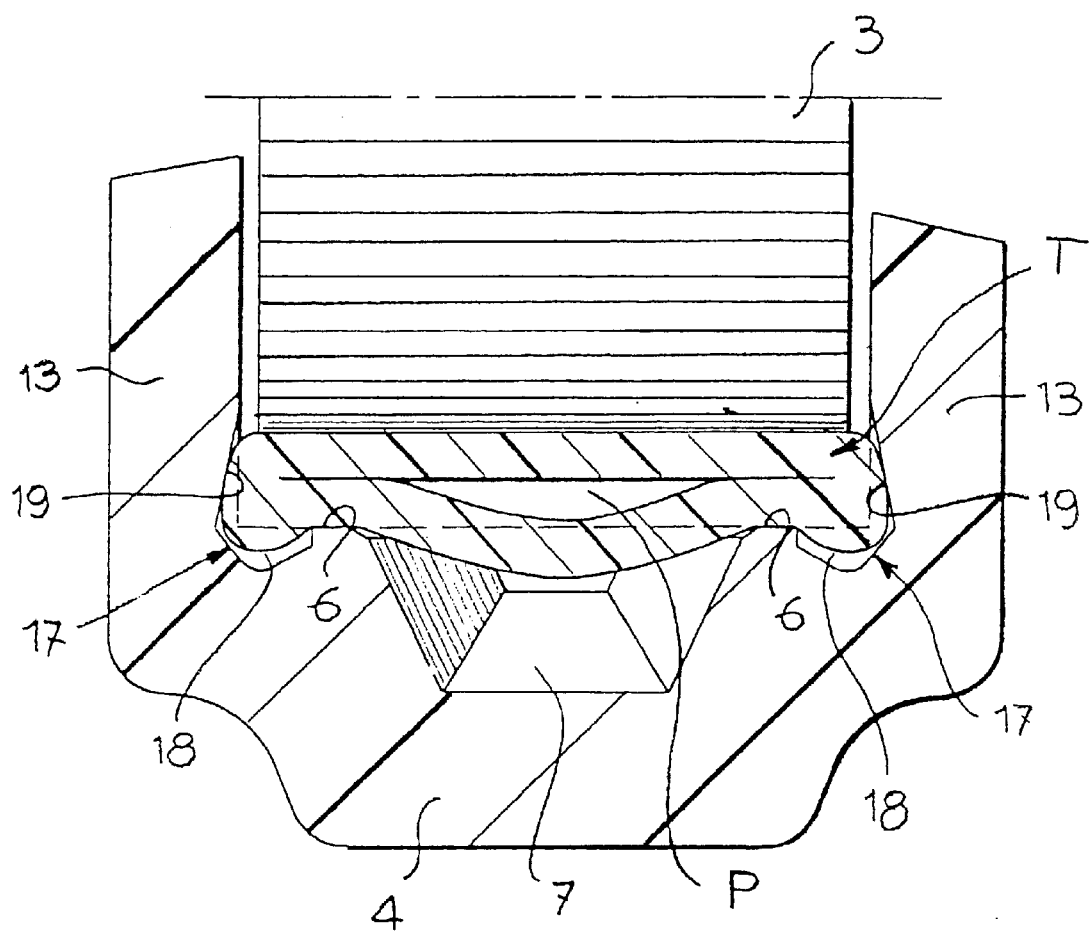

ROLLER CLAMP FOR REGULATING FLUID FLOW THROUGH AN ELASTICALLY DEFORMABLE TUBING

BACKGROUND OF THE INVENTION

The present invention is related to roller clamps for regulating the flow of a fluid through an elastically deformable tubing, particularly for infusion/transfusion devices in the medical field.

More particularly, the invention is directed to a roller clamp of the type comprising a generally channel-shaped body having two lateral walls and a bottom wall defining a clamping surface along at least part of which a central longitudinal groove is formed having an initial end and a terminal end and having a cross section which is decreasingly variable from said initial end towards said terminal end, and a roller rotatably supported by said lateral walls of the body and longitudinally displaceable in a guided fashion within said body substantially parallel to said clamping surface of the bottom wall so as to clamp in use an elastically deformable tubing fitted through the body between said bottom wall and said roller.

Roller clamps of the above referenced type are known for instance from U.S. Pat. No. 4,725,037 and U.S. Pat. No. 5,014,962.

When using such roller clamps the flow of the fluid along the elastically deformable tubing is adjusted by varying the longitudinal positioning of the roller along the clamping surface of the body bottom wall. The condition of minimum or null flow corresponds to positioning of the roller in correspondence of the terminal end of the longitudinal groove formed along the clamping surface of the bottom wall, whilst the condition of maximum flow corresponds to positioning of the roller in correspondence of the initial end of the longitudinal groove. This is evidently due to the fact that the section of the tubing, which is clamped and pressed between the roller and the portions of the clamping surface of the body bottom wall comprised between the central longitudinal groove and the lateral walls of the body itself, defines a restricted central passage for the fluid whose size depends upon the depth of the central longitudinal groove: evidently, the smaller the section of the central longitudinal groove is, the smaller is the cross section of such a passage, and vice-versa. In other words, as the roller is positioned more and more towards the terminal end of the longitudinal groove, the tubing is more and more strictly clamped and thus subjected to a more and more relevant elastic deformation. Since the tubing is normally made of thermoplastic material, or anyway of a material whose deformation takes place under constant volume, and since the space available for deformation thereof is limited on one side by the clamping surface of the bottom wall, on the other side by the roller, and sideways by the lateral walls of the body, the more the roller is shifted towards the terminal end of the central longitudinal groove, the more the space available for elastic deformation of the tubing is reduced. As a consequence the reaction to squeezing which is applied by the tubing against the roller progressively increases towards the terminal end of the longitudinal groove, which may require a remarkable effort to be applied by the operator to displace the roller towards and from said terminal end. This effort may quite become excessive and jeopardize the clamp operating capability.

This problem is particularly critical in case of tubings having relative thicker and thus harder walls.

SUMMARY OF THE INVENTION

A general object of the present invention is to give a solution to the above-referenced problem.

More particularly, the object of the invention is to provide a roller clamp of the type set forth at the beginning which is so designed that the force which is necessary to displace the roller even in the regions adjacent to the terminal end of the central longitudinal groove of the body clamping surface is kept within limits which are such as to anyhow ensure easy operation without requiring excessive efforts by the operator.

A further object of the invention is to provide a roller clamp of the type set forth in the beginning which is arranged, in a simple and economical fashion, so as to keep substantially even, or anyway within a relatively small variation range, the effort which is required to shift the roller along the whole extension of the central longitudinal groove of the body clamping surface.

According to the invention, these objects are achieved primarily by the fact that lateral longitudinal recesses are formed between the clamping surface of the bottom wall and the lateral walls of the body of the clamp, along at least part of said central groove, each lateral recess being defined in part by a depression of said bottom wall and in part by an undercut of the respective lateral wall.

These lateral longitudinal recesses define in practice auxiliary seats within which the lateral portion of the squeezed tubing can fit, thus accommodating elastic deformation thereof and drastically reducing the reaction applied by the tubing against the roller and, as a consequence, the effort which is necessary for displacement of the latter.

Said lateral recesses shall be occupied to a greater extent by the flattened ends of the tubing as the squeezed section thereof, i. e. the roller positioning, approaches the terminal end of the central longitudinal groove of the clamping surface of the body bottom wall. Each lateral recess may have a constant cross section, or an increasing cross section from the initial end towards the terminal end of the central longitudinal groove of the clamping surface of the body bottom wall. In either case each longitudinal recess may conveniently have a cross section provided with a non-symmetrically substantially U-shaped design arranged obliquely with respect to the body bottom wall.

Moreover each lateral recess may conveniently be arranged at a substantially lower level than said clamping surface, with its deepest portion substantially aligned with a corresponding end face of the roller.

BRIEF DESCRIPTION OF THE DRAWINGS

Additional features of the invention will become apparent in the following detailed description, with reference to the annexed drawings, purely provided by way of non limiting example, in which:

FIG. 1 is a diagrammatic perspective view of a roller clamp for medical use which constitutes one embodiment of the present invention, FIG. 2 is a cross-sectioned and enlarged view along line II—II of FIG. 4, FIG. 3 is a cross-sectioned and enlarged view along line III—III of FIG. 4, FIG. 4 is a lateral elevational and enlarged view of FIG. 1, FIG. 5 is a longitudinally sectioned view along line V—V of FIG. 4, FIG. 6 is a longitudinally sectioned view along line VI—VI of FIG. 1, and FIG. 7 shows in a larger scale a detail of FIG. 2 in the operating condition of the roller clamp according to the invention.

DETAILED DESCRIPTION OF THE INVENTION

Referring to the drawings, reference numeral 1 generally designates a roller clamp according to the invention, particularly designed for use in the medical field to adjust the flow of an infusion, transfusion or the like liquid along an elastically deformable tubing, designated as T in FIGS. 6 and 7.

The clamp 1 essentially consists of a body generally designated as 2 and of a roller or wheel indicated as 3, both conveniently made each in one piece of molded plastic material.

The body 2 has a generally channel-like shape with a bottom wall 4 and two lateral walls generally designated as 5.

The inner face of the bottom wall 4, i. e. the one facing towards the interior of the body 2, has over the maximum extent of its length a planar surface 6, which shall be indicated in the following as clamping surface. Along the major portion of this clamping surface 6 a central longitudinal groove 7 is formed which is defining along the clamp 1 a flow regulating region.

The central longitudinal groove 7 has an initial end 7a and a terminal end 7b, and its cross section is decreasingly variable from the initial end 7a to the terminal end 7b. As it can be better seen in FIGS. 2 and 7, this cross section of the groove 7 is substantially designed as an isosceles trapezoid having its shorter base placed at the bottom.

As it is well depicted in FIGS. 5 and 6, the clamping surface 6 of the bottom wall 4 is extending rearwardly beyond the terminal end 7b of the central longitudinal groove 7 and, at the end of the bottom wall 4, a transverse wall 8 is provided which is connecting the lateral walls 5 therebetween and delimits a rear passage 9.

In front of the initial end 7a of the central longitudinal groove 7, the bottom wall 4 has a clamping portion 10 merging into a resiliently openable attachment portion 11 formed by appendages 12 of the lateral wall 5 in correspondence of the front end of the body 2.

Along the clamping surface 6 of the bottom wall 4, and in correspondence of the flow control region defined as already explained by the clamping surface 6, each lateral wall 5 has a lower section 13 connected to the bottom wall 4 and an upper section 14 delimiting internally a channel 15 which is extending substantially parallel to the clamping surface 6.

The two channels 15 formed by the upper portions 14 of the two lateral walls 5 define respective longitudinal guides in which two axial pins 16, projecting from opposite sides of the roller 3, are freely rotatably and slidably fitted.

As it can be seen in FIGS. 5 and 6, the guides 15 extends along the whole length of the central longitudinal groove 7 and continue beyond the terminal end 7b thereof, ending at a certain distance from the transverse wall 8. The roller 3 is longitudinally movable over the entire extension of the guides 15 which are thus delimiting, along with the central longitudinal groove 7 and the clamping surface 6 arranged an opposite side of this groove 7 and rearwardly of the terminal end 7b thereof, said flow control region.

According to the fundamental feature of the present invention, two lateral longitudinal recesses 17 are formed between the clamping surface 6 and the lower sections 13 of the lateral walls 5, along at least part and more conveniently over the whole extension of the central longitudinal groove 7. Each of the lateral recesses 17, which in the case of the shown example are extending up to the front end of the body 2, is defined (as shown in better detail in FIG. 7) partly by a depression 18 of the bottom wall 4, and for the remaining part by an undercut 19 of the lower section 13 of the respective lateral wall 5, which in that area has thus a reduced thickness.

In the case of the shown example, the transverse section of each lateral recess 17 has a non-symmetrical substantially U-shaped profile, arranged obliquely with respect to the bottom wall 4 of the body 2. The bottom of this U-shaped cross section of each lateral recess 17 is extending down to a substantially lower level with respect to the level of the clamping surface 6 comprised between the central longitudinal groove 7 and the corresponding lateral wall 5. Moreover the deepest area of the bottom of each lateral recess 17 is aligned with the corresponding end face of the roller 3.

In the case of the shown example the cross section of each lateral recess 17 is even, i.e. constant: however, according to an alternative embodiment not shown in the drawings, this section may instead be progressively increasing towards the terminal end 7b of the longitudinal groove 7.

In use the elastically deformable tubing T, normally made of a thermoplastic material, is fitted into the body 2 through the passage 9 and the front end thereof, between the clamping surface 6 and the roller 3. If the roller 3 is positioned in front of the initial end 7a of the central longitudinal groove 7, i. e. in the areas of the two guide channels 15 corresponding to the slanting part 10 of the bottom wall 4, the tubing T is practically undeformed, whereby no adjustment of the liquid flow therewithin is performed. To regulate the liquid flow, the roller has to be displaced in correspondence of the initial end 7a and then towards the terminal end 7b of the longitudinal groove 7. The tubing T is thus elastically deformed into a substantially flattened condition between the roller 3 and the clamping surface 6, such as shown in FIG. 7, however keeping a central open passage P whose width is directly proportional to the size of the transverse section of the central longitudinal groove 7. In other words the size of the central passage P, and thus the flow rate of the liquid along the tubing T, is larger as the roller 3 is positioned in proximity or in correspondence of the initial end 7a of the central longitudinal groove 7, and is progressively reduced as the roller 3 is brought near to the terminal end 7b. If the roller 3 is further displaced beyond the terminal end 7b of the central longitudinal groove 7, the tubing T is squeezed in a completely flattened condition, whereby the fluid flow is interrupted.

The longitudinal recesses 17 provided, according to the invention, along the flow control region, i. e. at opposite sides with respect to the central longitudinal groove 7, in practice perform the task of housings accomodating the elastic expansion of the sides of the tubing T clamped and pressed between the roller 3 and the clamping surface 6. Obviously this expansion is greater as the roller 3 is close to the terminal end 7b of the central longitudinal groove 7: thus in practice the lateral recesses 17 shall be only partially filled by the flattened sides of the tubing T while the latter is clamped by the roller 3 in areas near to the initial end 7a, and shall be more and more completely occupied thereby as the clamping area gets closer to the terminal end 7b of the central longitudinal groove 7.

The possibility of lateral expansion of the clamped tubing T, such as afforded by the provision of the two lateral recesses 17 according to the invention, prevents that any excessive elastic reactions, which might negatively affect operation of the clamp, be transmitted by the clamped tubing T to the roller 3. Thus in practice the manual effort required to displace the roller 3, even towards and from positionings thereof corresponding to the terminal end 7b of the central longitudinal groove 7, is appreciably reduced as compared with the roller clamps according to the prior art.

Naturally, the details of construction and the embodiments may be widely varied with respect to what has been described and illustrated, without thereby departing from the scope of the present invention such has defined in the appended claims.

What is claimed is:

1. A roller clamp for regulating fluid flow through elastically deformable tubing, comprising a generally channel-shaped body having two lateral walls and a bottom wall defining a clamping surface along at least part of which a central longitudinal groove is formed having an initial end and a terminal end and having a cross section which is decreasingly variable from said initial end towards said terminal end, and a roller rotatably supported by said lateral walls of the body and longitudinally displaceable in a guided fashion within said body substantially parallel to said clamping surface of the bottom wall so as to clamp in use an elastically deformable tubing fitted through the body between said bottom wall and said roller, wherein lateral longitudinal recesses are formed between said clamping surface of said bottom wall and said lateral walls of said body, along at least part of said central longitudinal groove, each lateral recess being defined in part by a depression of said bottom wall and in part by an undercut of the respective lateral wall.

2. Roller clamp according to claim 1, wherein said lateral longitudinal recesses have a constant cross-section.

3. Roller clamp according to claim 1, wherein said lateral longitudinal recesses have an increasing cross-section from said initial end towards said terminal end of said central longitudinal groove.

4. Roller clamp according to claim 1, wherein said lateral longitudinal recesses are provided a long the whole extension of said central longitudinal groove.

5. Roller clamp according to claim 1, wherein said undercut of each lateral wall is defined by a thickness reduction of said lateral wall.

6. Roller clamp according to claim 1, wherein each lateral longitudinal recess has a cross-section having a non-symmetrical substantially U-shaped design arranged obliquely with respect to said bottom wall of said body.

7. Roller clamp according to claim 6, wherein said clamping surface is located at a respective level and each lateral recess is provided at a substantially lower level than said level of said clamping surface.

8. Roller clamp according to claim 6, wherein said roller has opposite end faces and each said lateral recess has a deepest portion which is substantially aligned with one corresponding end face of said roller.

* * * * *